United States Patent [19]

Cohn

[11] Patent Number: 5,101,804

[45] Date of Patent: Apr. 7, 1992

[54] BIOLOGICAL FLUID WARMER

[75] Inventor: William E. Cohn, Houston, Tex.

[73] Assignee: Baylor College of Medicine, Houston, Tex.

[21] Appl. No.: 579,003

[22] Filed: Sep. 4, 1990

[51] Int. Cl.$^5$ .............................. F24J 1/00; F61F 7/00; A61J 1/05

[52] U.S. Cl. ..................................... 126/263; 126/204; 62/4; 604/113; 128/898; 128/400; 165/104.17

[58] Field of Search ............. 126/263, 204, 205, 207; 62/4; 604/113, 4, 408; 128/399, 400, 898, DIG. 2; 165/104.15, 104.17

[56] References Cited

U.S. PATENT DOCUMENTS

| | | | |
|---|---|---|---|
| 4,265,216 | 5/1981 | Marshall et al. | 126/623 |
| 4,430,988 | 2/1984 | Krasberg | 126/263 X |
| 4,464,563 | 8/1984 | Jewett . | |
| 4,784,217 | 11/1988 | Payre et al. . | |
| 4,880,415 | 11/1989 | Urakami . | |
| 4,934,336 | 6/1990 | White | 126/263 |

FOREIGN PATENT DOCUMENTS 59-198686  7/1988  Japan .

OTHER PUBLICATIONS

PCT International Publication No. WO 90/07947 International Publication Date: Jul. 26, 1990 (International Application No. PCT/US90/00176 International Filing Date: Jan. 18, 1990).

*Primary Examiner*—Larry Jones
*Attorney, Agent, or Firm*—Fulbright & Jaworski

[57] ABSTRACT

The present invention relates to a device and method for warming biological fluids. The portable self-contained device which warms physiological fluids including blood is comprised of a reaction container which is capable of storing at least one chemical which when mixed with a second chemical will produce an exothermic chemical reaction, a mixing means for mixing the two chemicals to produce the exothermic chemical reaction, a heat exchanger to absorb heat from the exothermic reaction and transfer it to the physiological fluid or blood, a temperature regulating means to regulate the maximum temperature of the device and an insulating container for enclosing the reaction means, heat exchanger and temperature regulating means. The method of rapidly heating the stored cold physiological fluids including blood to about 39° during infusion comprise the step of activating the physiological fluid warming device by mixing the chemicals to produce the exothermic chemical reaction and passing the physiological fluid or blood through the heat exchanger.

20 Claims, 8 Drawing Sheets

BIOLOGICAL FLUID WARMER

FIELD OF THE INVENTION

This invention relates to devices for the rapid heating of physiological fluids prior to injection into humans. More particularly, the invention is a self-contained apparatus for warming blood to 35°–40° C. before introducing the blood into a patient.

BACKGROUND OF THE INVENTION

In many medical practices it is necessary or desirable to heat a fluid before it is administered to a patient. For example, fluids such as whole blood and packed cells are stored in refrigerators at temperatures of approximately 4° C. These fluids are often required to be administered to a patient within a short period of time after removal from the refrigerator. Rapid transfusion of cold blood often leads to systemic hypothermia. Because of the nature of the illness, trauma or medical intervention, many patients needing blood may already be hypothermic. The infusion of cold blood only adds additional insult to an already weakened system.

There is room for a limited number of trained medical personnel in the shock room. These individuals are involved in the flurry of activity that accompanies the arrival of a seriously injured or hypovolemic patient in the emergency center. (Maintaining an airway, assessing the patient, obtaining a history, establishing venous access etc.) As a result, crucial warming of blood and other hypothermic fluids is often delayed, or neglected entirely. In addition, the quickest electrical blood warmers take 5-10 minutes to reach operating temperature, which compounds the delay.

Great care must be exercised when heating certain physiological fluids in order to avoid damaging the cells by exposing them to too high a temperature. For example, whole blood or packed cells are damaged by high temperatures, and certain medicaments which might be in physiological solutions are sensitive to exposure to high temperatures. Thus, these conditions severely restrict the techniques used to quickly warm refrigerated or cooled physiological fluids.

Currently, apparatuses for warming physiological fluids, including blood, utilize either rapidly flowing hot water or electric heating elements as the source of thermal energy. These systems require large and/or complex equipment and skilled technical personnel for their operation. Additionally, the equipment usually requires a large amount of space, a commodity often limited in emergency situations.

The need for electricity makes currently available blood warmers inapplicable for use in the field and during pre-hospital transport, when the crucial initial steps of recussitation are carried out. This failure to warm the crystalloid volume expanders used during this phase of care initiates the steady drop in core body temperature seen in patients suffering from hypovolemic shock. Furthermore, conventional fluid warming must be discontinued for transport of the patient from the emergency center to the operating room.

There are reports of using exothermic or endothermic reactions to change the temperature of physiological solutions prior to injection. However, these reports provide no method to regulate the temperature. Furthermore, the systems described were designed to warm or cool small fixed amounts of injectable solutions, and could not be used to warm a continuous infusion.

Thus, it would be desirable to provide a device for warming physiological fluids which is compact, rapid, easy to use, does not require electrical input during its use and is self-contained and disposable.

SUMMARY OF THE INVENTION

The object of the present invention is to provide a portable self-contained device for warming physiological solutions.

An additional object of the present invention is to provide a device for warming fluids with energy produced by an exothermic chemical reaction.

Another object of the present invention is to provide a method of rapidly heating cold physiological solutions with a portable device that requires no external source of power prior to infusing the solution into a patient.

Thus, in accomplishing the foregoing objects, there is provided in accordance with one aspect of the present invention, a portable self-contained device for warming physiological fluids comprising: a reaction container capable of storing at least one chemical to produce an exothermic chemical reaction; a mixing means for mixing at least a pair of chemicals to initiate said exothermic chemical reaction within said reaction container; a heat exchanger open at each end, said heat exchanger having an inlet and an outlet, and being sufficiently close to the reaction container to absorb the heat from the exothermic reaction and transfer said heat to the physiological fluid; a temperature regulatory means in intimate contact with said heat exchanger and said reaction container to regulate the maximum operating temperature; and an insulating container for enclosing said reaction container, mixing means, heat exchanger and temperature regulatory means, said insulating container having an inlet port and an outlet port, wherein the inlet of the heat exchanger passes through the inlet port and the outlet of the heat exchanger passes through the outlet port.

In a further aspect of the present invention, the temperature regulating means includes a composition of matter that undergoes a phase change at a temperature between about 32° C. to 39° C. This composition of matter can be selected from the group consisting of waxes, polymers and crystalline solids.

A wide variety of chemicals can be used for the exothermic reaction. In a preferred mode, it is found that water and anhydrous calcium carbonate or water and anhydrous calcium chloride or water and anhydrous calcium oxide or water and anhydrous sodium hydroxide generate sufficient heat and yet constitute no biohazard. It should be noted, however, that exothermic reactions are quite common, and the selection of possible reagents is almost limitless.

A further aspect of the present invention is a method for heating blood to about 38° C. prior to infusion into a patient, comprising the steps of mixing at least a pair of chemicals to produce an exothermic chemical reaction in the previously described device and passing the physiological fluid through the heat exchanger. In the preferred embodiment the physiological fluid is blood.

Other and further objects, features and advantages will be apparent from the following description of the presently preferred embodiments of the invention given for the purpose of disclosure when taken in conjunction with the accompanying drawings.

BRIEF DESCRIPTION OF THE DRAWINGS

The drawings are not necessarily to scale. Certain features of the invention may be exaggerated in scale or shown in schematic form in interest of clarity and conciseness.

DESCRIPTION OF THE PREFERRED EMBODIMENT

It is readily apparent to one skilled in the art that various substitutions and modifications may be made to the invention disclosed herein without departing from the scope and spirit of the invention.

Figure 1:
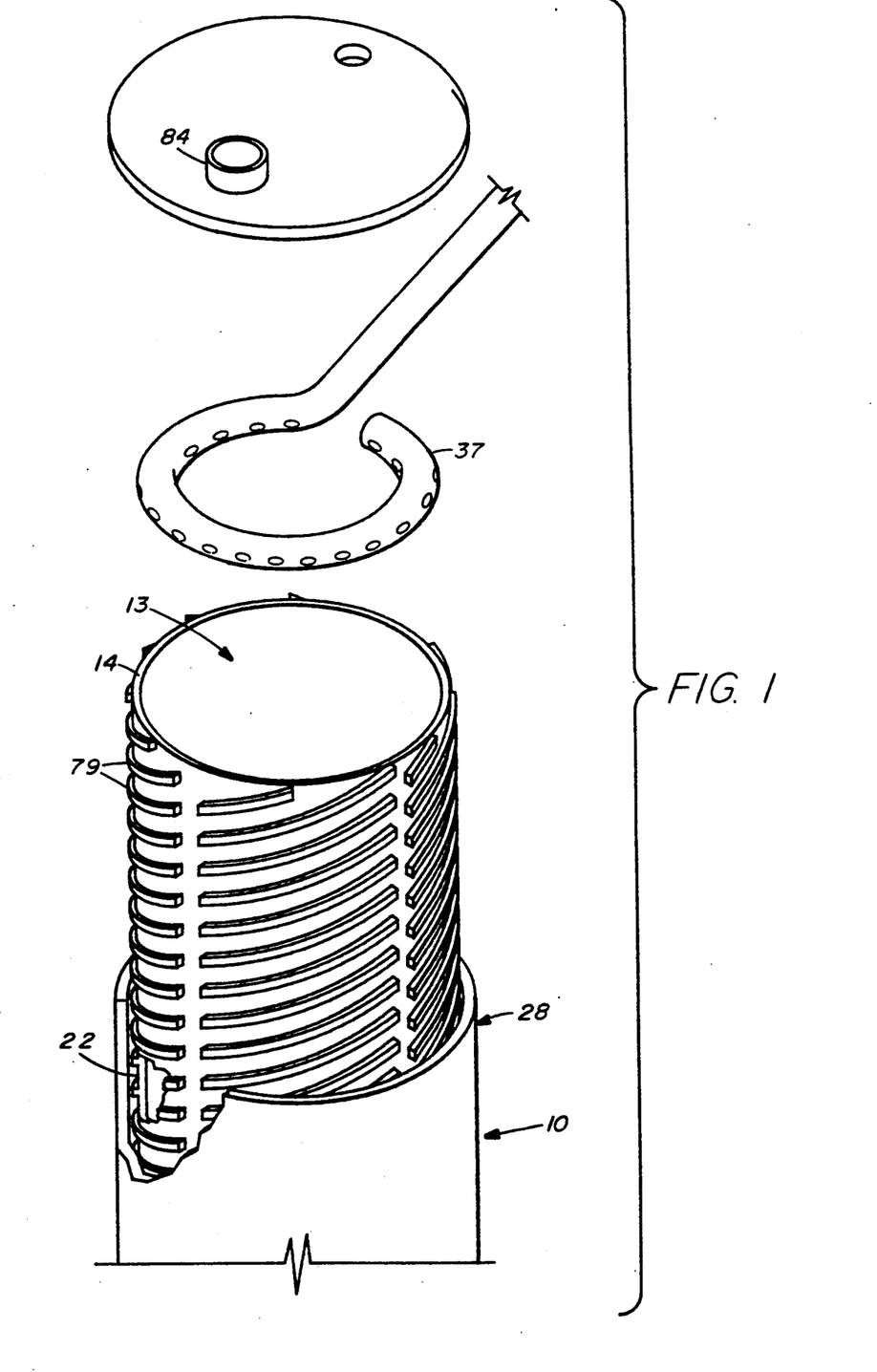
FIG. 1 shows a diagramatic view of one embodiment of the fluid warming apparatus that uses an anhydrous salt and water to initiate the exothermic reaction.
Figure 2:
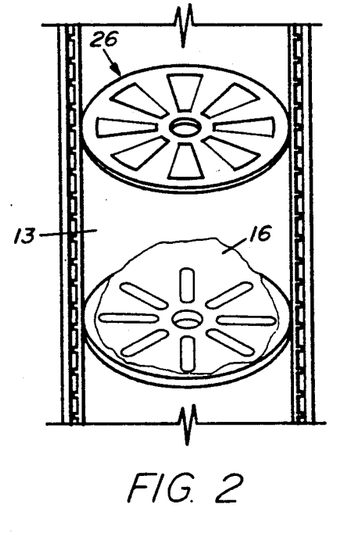
FIG. 2 is a diagramatic partial cutaway showing the position of the reaction container partitions.

One embodiment of the present invention is seen in FIG. 1. This embodiment includes a portable self-contained device 10 for warming a physiological fluid comprising a reaction container 13 capable of storing at least one chemical 16, said chemical producing an exothermic chemical reaction when mixed with another chemical 17. A mixing means 19 for mixing at least a pair of said chemicals 16 and 17 to produce said exothermic chemical reaction within said reaction container 13. A heat exchanger 22 with an inlet 37 and outlet 40, to said heat exchanger 22 sufficiently close to said reaction container 13 to absorb heat from said exothermic reaction and transfer said heat to the physiological fluid. There is also a temperature regulatory means 25, wherein said temperature regulatory means 25 is in intimate contact with the heat exchanger 22 and reaction container 13 and regulates the maximum operating temperature. The temperature regulating means 25 is necessary to prevent overheating and destruction of blood of other labile solutions. The device 10 also includes an insulating container 28 for enclosing said reaction container 13, mixing means 19, temperature regulatory means 25 and heat exchanger 22, said insulating container 28 having an inlet port 31 and an outlet port 34 wherein the inlet 37 of the heat exchanger 22 passes through the inlet port 31 and the outlet 40 of the heat exchanger 22 passes through the outlet port 34.

One skilled in the art will readily recognize that the reaction container 13, heat exchanger 22 and temperature regulatory means 25 can each be designed in a variety of shapes and ways to facilitate rapid yet controlled warming of infusable cold fluids. Before describing the preferred embodiment of the three components, it will be useful to consider the function of each.

The reaction container 13 in which the exothermic reaction takes place is a closed container which does not allow contact between its contents 16 and 17 and the infusable fluid. It is, however, constructed of a thermally conductive material that readily allows exchange of heat between the reaction container 13 and infusable fluid. Ideally, it has a large central lumen to facilitate rapid mixing of the exothermic reaction chemicals 16 and 17 and dispersal of the resultant heat. It should have ample surface area for heat transfer to take place between its contents, the heat exchanger 22 and the temperature regulatory means 25. Finally, it is constructed so that the chemicals can be mixed and the reaction initiated in a simple fashion.

The heat exchanger 22 is a sterile conduit through which the cold fluid flows and is warmed in the process. A large surface area is essential to provide easy transfer of heat from the reaction container 13 to the infusable fluid. The heat exchanger 22 is preferably designed to allow ample time for cold fluid to be warmed as it flows through this conduit, even at high flow rates. The resistance of the heat exchanger should be small to allow the high flow rates needed to recussitate the actively bleeding patient in hypovolemic shock.

The temperature regulatory means 25 is designed to prevent the fluid from reaching temperatures of greater than 40° C. In the case of blood, higher temperatures can cause denaturation of plasma proteins, lysis of cells, and irreversible damage. Exothermic reactions, as a group, proceed with extreme predictability. For any given amount of reagents, a fixed reproducible amount of energy is produced.

One skilled in the art will readily recognize that several different types of heat exchangers 22 satisfy the high flow, high surface area, low resistance constraints. Three most desirable are the coaxial cylinder (FIGS. 1-5), the helix (FIGS. 7-9) and the multiple small tubes variation (FIGS. 10-14).

The Coaxial cylinder (FIGS. 1-5) is the preferred embodiment and consists of a central cylinder 14 housing the reaction container 13, surrounded coaxially by a second cylinder 28 of insulating material such that the walls of the two cylinders are separated by about 0.5-1 mm. The small space between these two cylinders serves as a conduit 22 through which the physiological fluids flow. For example, blood would flow in a thin sheet 22 around the outside of the cylinder 28 housing the reaction container 13.

In the helix variants (FIGS. 7-9) a coiled tube 22 is wrapped around the outside of the reaction container 13 and serves as a conduit 22. In the multiple small tubes variant (FIG. 10-14), several small conduits 22 pass through the reactants 16 and 17 in the reaction container 13.

Similarly, several types of reaction containers 13 can be designed. The simplest would consist of a hollow metal cylinder in which one or both reactants are arranged such that intermixing is prevented until the blood warmer is activated.

Figure 6:
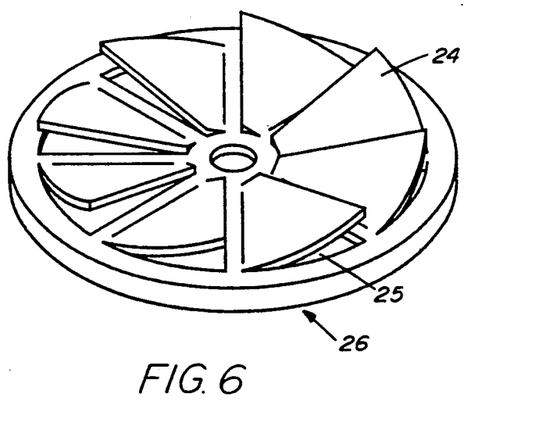
FIG. 6 is an alternate design for a reaction vessel partition.

In one embodiment (FIGS. 1-5, 8, 9 and 13), the cylinder 14 is divided into multiple chambers 52 by circular partitions 26 made of aluminum screen or other porous heat conducting material. On each of these partitions would be a portion of one of the reagents 16. In the preferred embodiment the reagent is granular anhydrous calcium chloride 16. To activate the blood warmer, the second reagent, water 17, would be poured into the cylinder. The partitions 26 provide increased surfaced area and better distribution of reagents. They also serve as heat sinks to improve transfer of the thermal energy from the center of the reaction container to the walls, where the heat exchange is taking place. In one embodiment (FIGS. 4 and 6), the partitions 26 include aluminum and temperature regulating means 25. The temperature regulatory means 25 can coat the partitions 26 or can be sandwiched between two aluminum layers. Fins 24 can be added to facilitate heat transfer.

The reaction container 13 is designed to facilitate release of additional packets of reagent 16 some time after the blood warmer is activated to decrease thermal leaching.

Other design features include a mechanical mixing means 19 to provide rapid mixing of reagents as well as to prevent establishment of thermal gradients within the reaction container 13. In the preferred embodiment (FIG. 11), the partitions 26 are turbine shaped and mounted on a central axial 85 running the length of the reaction vessel such that they can be rotated. Rotation, for example, can be by use of a hand crank 82 on the top of the blood warmer 12.

The temperature regulatory means 25 lends itself to an almost limitless number of possible designs. In the preferred embodiment, icosane wax 25 is incorporated into the metal partitions 26 by sandwiching the material between two thin layers of metal. Alternatively, the substance can be incorporated in hollow metal vanes or hollow metal tubes within the lumen of the reaction container, or even within the container wall itself.

Without the temperature regulation means 25 the energy required to adequately heat 6 units of blood, when released in the reaction vessel at once, would have temperatures far in excess of the allowed 40° C., and the blood would be destroyed as it passed through the heat exchanger 22. One example of the temperature regulatory means is a phase-change buffer which can be selected from a wide variety of substances including waxes, polymers and crystalline solids. The exact temperature is determined by the phase change temperature (for example, melting point) of the compound chosen. The compound is incorporated into the warmer 10 in such a fashion so as to maximize the area of contact between it and both the reaction container 13 and the heat exchanger 22. Thus, heat exchange can occur freely between all three components.

The temperature regulatory means 25 in the device of the present invention consists of a composition of matter with a melting point between about 32° to 39° C. One skilled in the art will readily recognize various ways to integrate the substance into the device to maximize contact with both the heat exchanger 13 and the reaction container 22.

When the exothermic reaction is initiated, the temperature rises rapidly until it reaches the melting point of the phase change buffer in the temperature regulatory means 25. At the melting point, the substance undergoes a phase change, and in so doing, becomes an energy sink. As the exothermic reaction proceeds and energy is rapidly liberated, more of the regulatory substance undergoes a phase change, The temperature of the device, however, remains at the melting point of the substance between about 32° to 39° C. until all of the substance has melted. The amount of the phase change buffer can be adjusted to insure that the device does not overheat.

In one preferred embodiment of the device (FIG. 8), the reaction container consists of tube of aluminum foil wrapped around an internal skeleton of plastic or screen mesh designed with partitions 26 into the lumen of the reaction container 22 creating a series of stacked compartments 52. These partitions 26 serve to dispense the reactants through out the reaction container 13 to insure rapid and uniform mixing of the reactants when they are combined. For example, the first reactant 16 can be dispersed throughout the reaction container and the second reactant 17 added to the reaction container when ready to use. Examples of first reactants 16 are anhydrous sodium hydroxide, anhydrous calcium carbonate, anhydrous calcium chloride and anhydrous calcium oxide. For all of these compounds, water is used as the second reactant 17.

Figure 8:
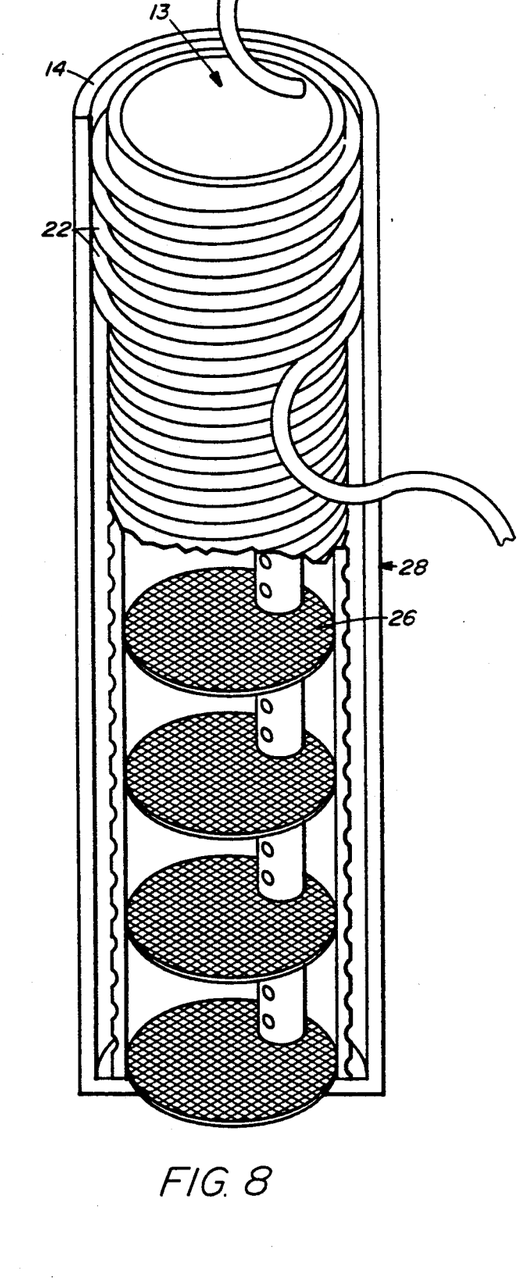
FIG. 8 is an alternate design of the heat exchange container.
Figure 9:
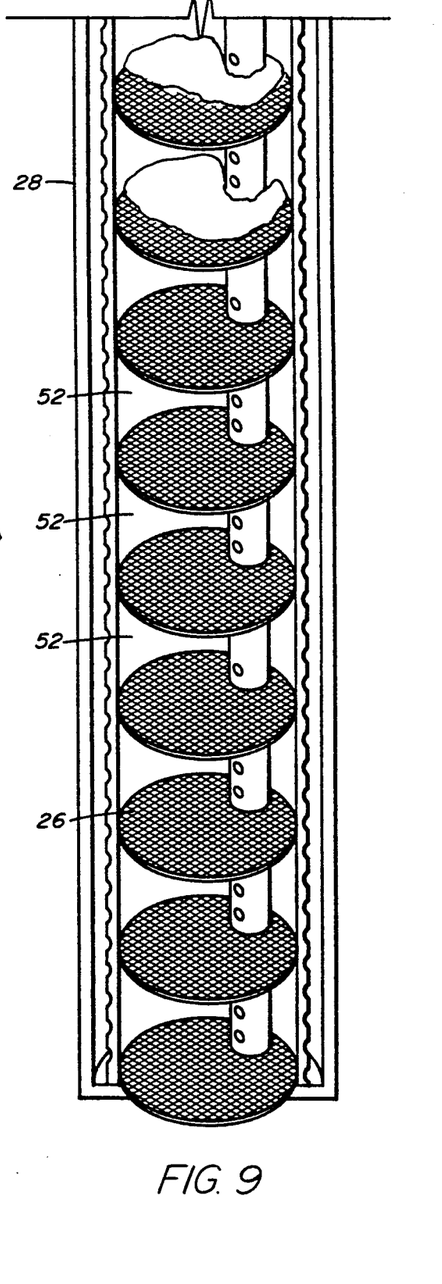
FIG. 9 is a schematic cut-away showing the partitions and chambers.
Figure 10:
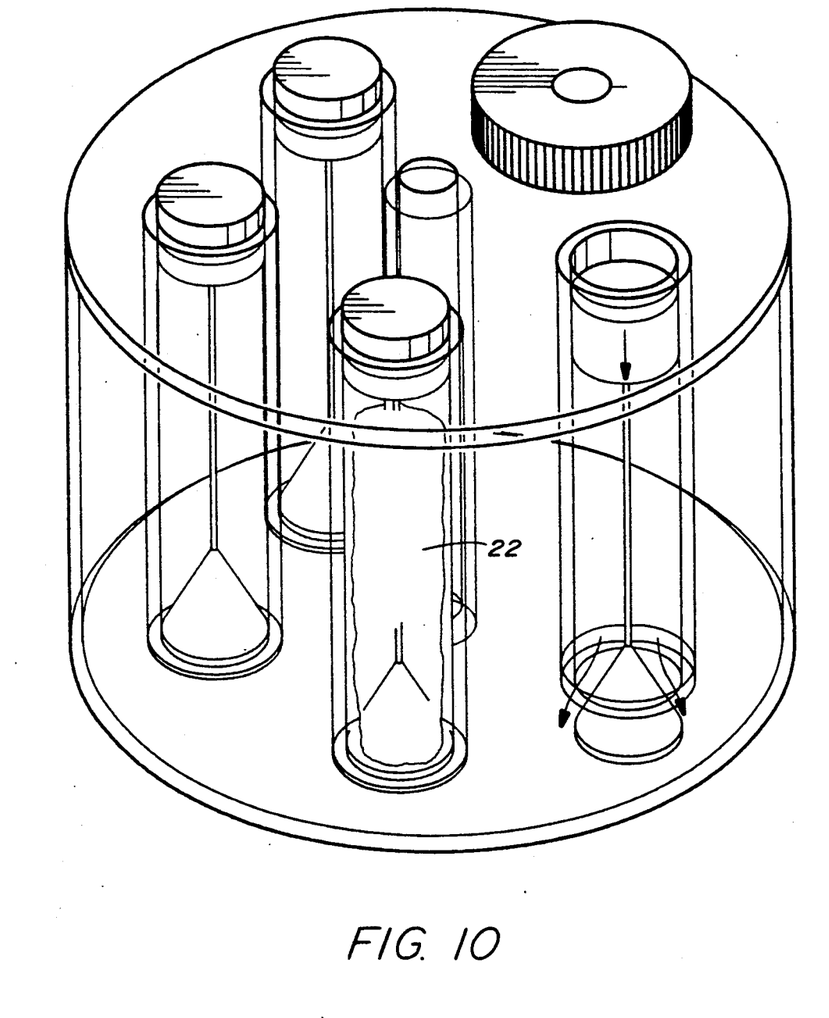
FIG. 10 shows a diagramatic view of a device with multiple chambers and the ability to add additional reagents to the reaction container at intervals after initiation.
Figures 11, 12:
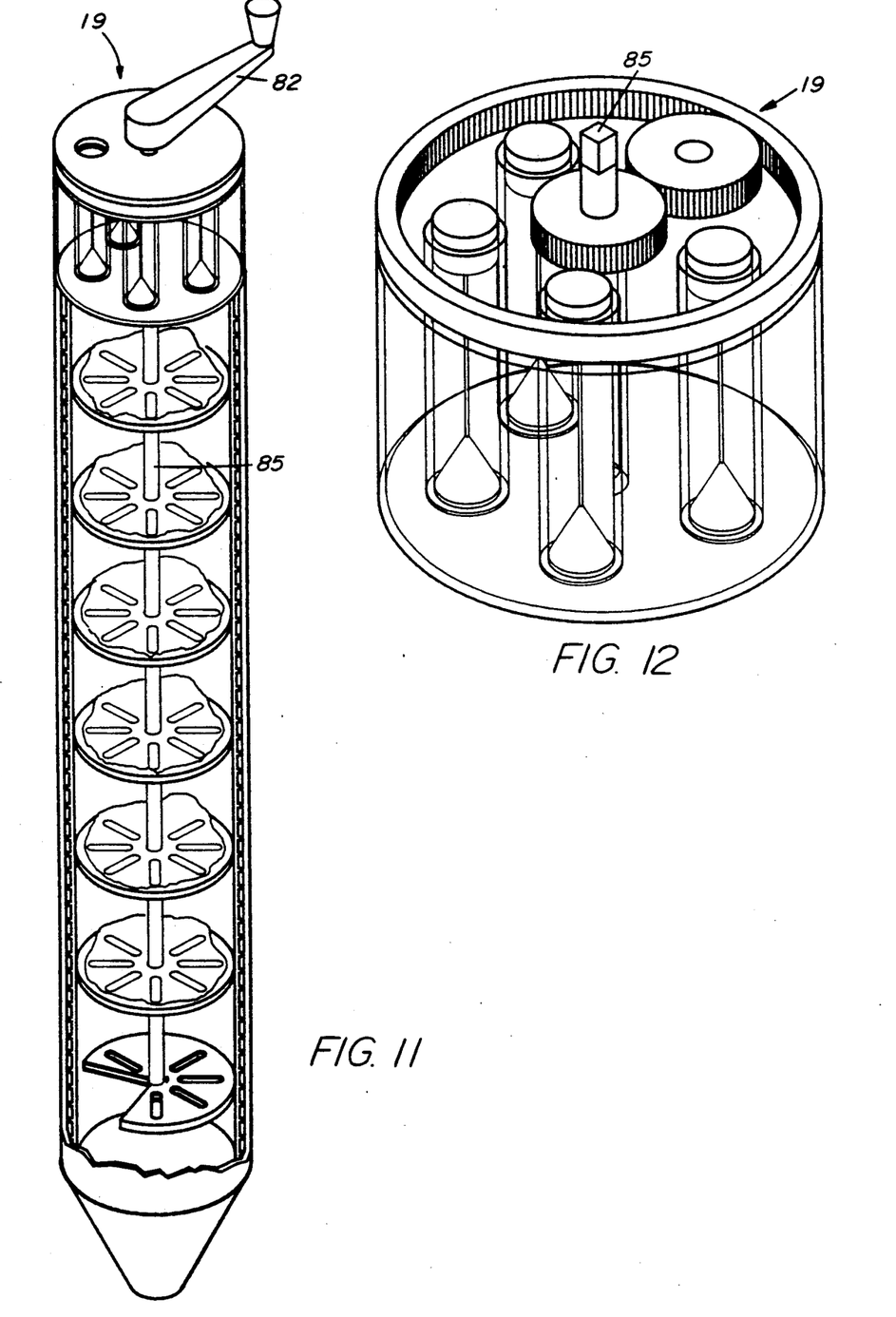
FIG. 11 shows a schematic view of one container of the multiple container device.
FIG. 12 is an exploded view of a means for mixing and for rotating multiple containers.
Figure 13:
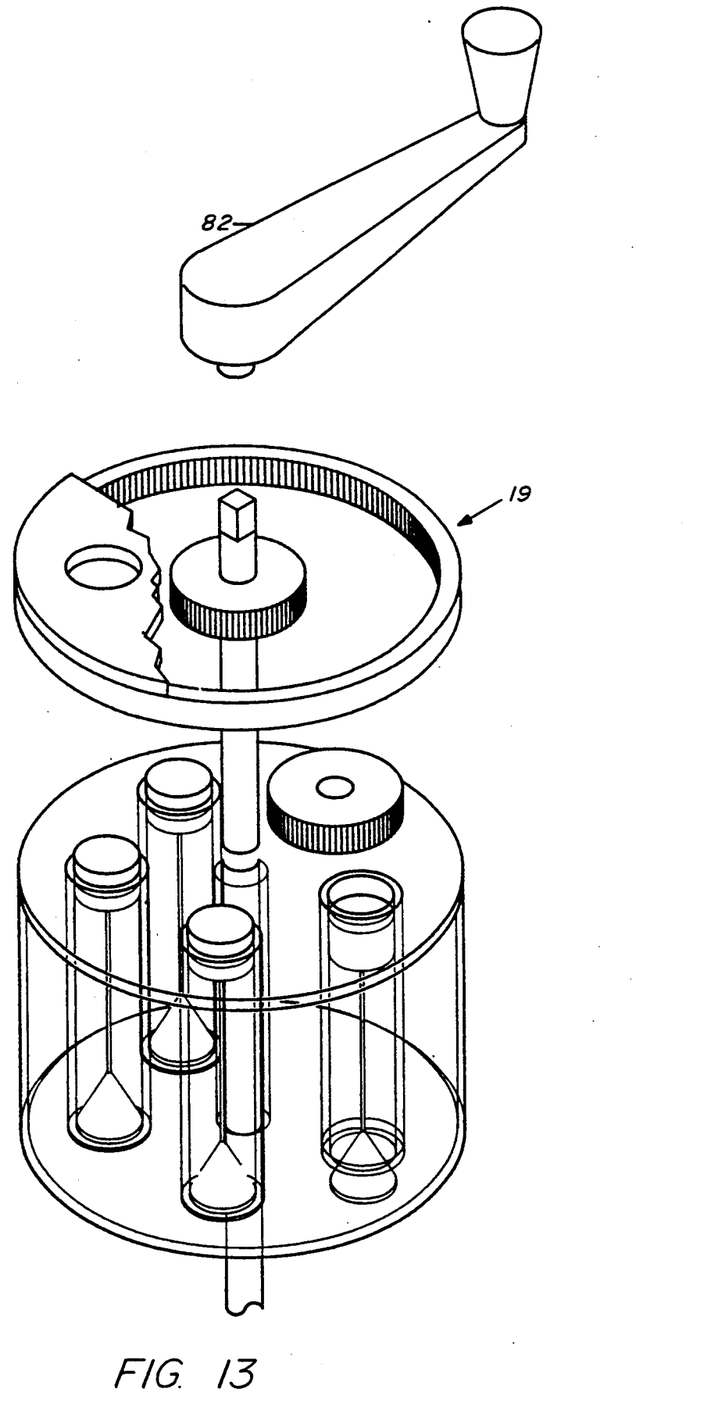
FIG. 13 is an exploded view of the mixing means and rotating means for adding additional reagents.
Figure 14:
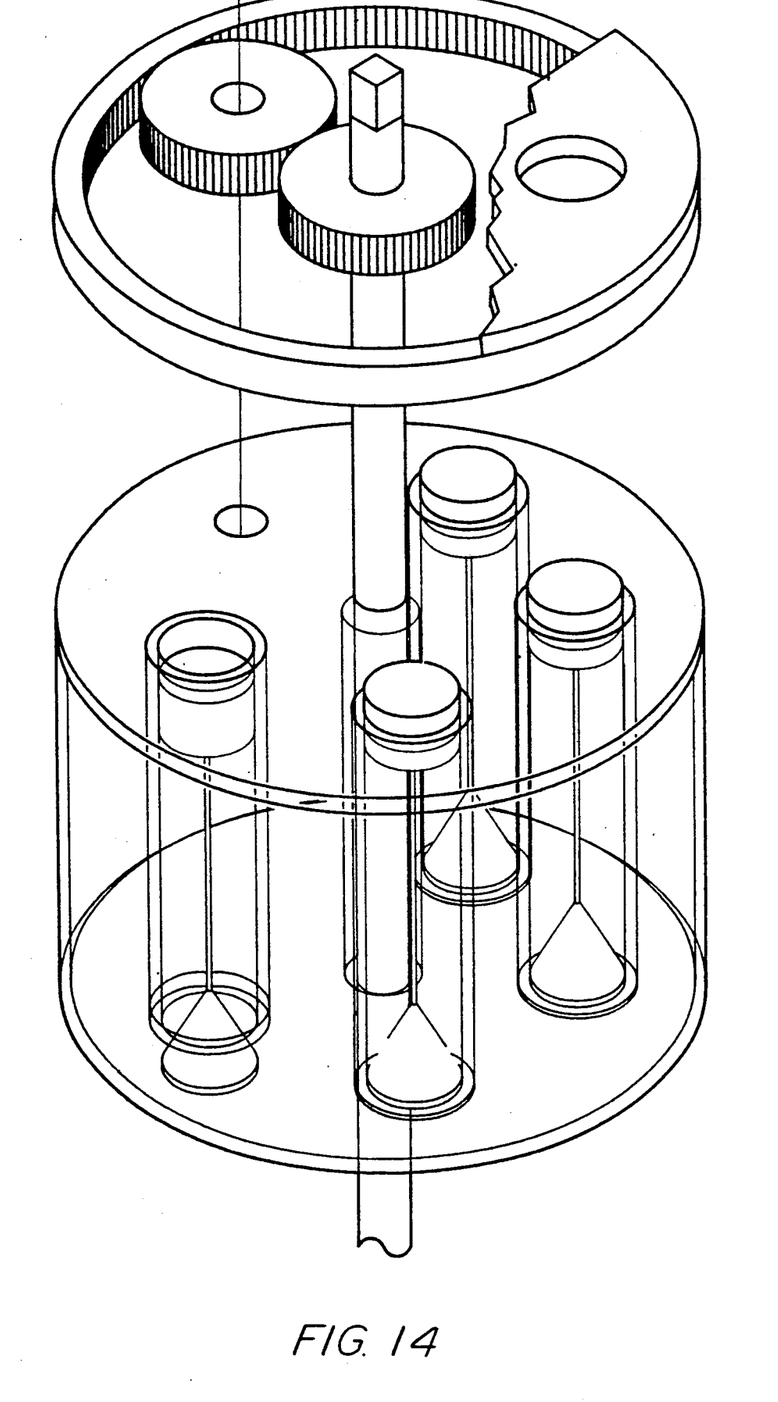
FIG. 14 is an exploded view of the device.

Surrounding the reaction container is about a 2 to 5 mm layer of temperature regulatory means 25. On top of this layer is a second layer of aluminum foil 25. The two layers of foil could be corrugated to increase the surface area and contact between the aluminum shells and the temperature regulatory means 25.

Closely applied to the outer shell of aluminum foil would be a thin layer of sterile plastic. The plastic is chosen to be chemically inert, blood compatible, and sufficiently thin to allow heat transfer. The outermost layer consists of a thermally insulating shell 28, lined by an inert, blood compatible layer of plastic on its inner surface. The two cylindrical layers of blood compatible plastic are positioned coaxially with a gap of about 0.5 to 1 mm between them. Physiological fluid flows through this gap and is heated prior to infusion. This conduit represents the heat exchanger 22.

In the preferred embodiment the temperature regulating means 25 includes a composition of matter that undergoes a phase change at a temperature between about 32° to 39° C. It is known in the art that various waxes, polymers and crystalline solids when exposed to heat in the range of about 32° to 39° C. will change from a solid phase to a liquid phase. Upon cooling below the temperature of change, they will revert to the solid phase. This change in phase absorbs the extra energy generated by the exothermic reaction and thus provides a "thermal clamp.". Some examples of these waxes, polymers and crystalline solids include icosane wax, serine wax, and naphthenes. In the preferred embodiment of the present invention, icosane wax is used.

In the preferred embodiment the composition of the temperature regulating means is coated around the reaction container 13 covering all of the spaces and providing a layer between the reaction container 13 and the heat exchanger 22 and extends throughout the surface between the heat exchanger 22 and the insulating container 28. Thus, when the exothermic reaction begins, a large amount of heat is released melting the thermoregulating composition; however, the thermo-regulating composition has sufficient capacity to absorb all this heat and maintain a temperature in the 32° to 39° C. As the cool fluid is passed through the heat exchanger 22, heat is absorbed by the fluid and thus warmed. When the fluid removes heat from the temperature regulating means 25, the composition of matter reverts to its solid phase. As the exothermic reaction proceeds, and the heat is removed to warm the fluid, the temperature regulating means 25 moves between the solid and liquid phase, regulating the amount of heat which is released into the blood. It is this regulating mechanism which makes the invention practical. Without this regulating mechanism, the temperature would rise above 40° C. damaging the physiological fluids, especially blood.

One skilled in the art will readily recognize that a variety of chemicals or compounds can be used to generate the exothermic reaction. For instance, it is known that if water is added to any one of the anhydrous salts of calcium carbonate, calcium oxide, calcium chloride or sodium hydroxide, heat is produced. In the preferred embodiment calcium chloride is used because it produces non-toxic compounds when water is added.

In the present invention any physiological fluid can be used, although blood is the preferred fluid. For example, blood is taken from the cold storage, the exothermic chemicals are mixed to generate the heat and the blood is then pushed through the heat exchanger 22. As it exits 40 the heat exchanger 22, it can be administered to the patient.

One embodiment of the infusible fluid warmer 10 consists of an aluminum cylinder 14 measuring 40 to 60 cm in length and 7 to 10 cm in diameter, with a wall thickness of 0.5 to 1 mm. The cylinder 14 is sealed on both ends, except for a small valved port 84 on one end that allows the cylinder 14 to be filled with water 17, while preventing accidental spillage of cylinder contents. At 5 cm intervals, the cylinder is partitioned by aluminum discs 26. The discs are cut and bent into turbines 24. The ten or so separate compartments 52 created by the partitions 26 each contain 50 grams of granular anhydrous calcium chloride 16. Each turbine-shaped partition 26 has a disc of fabric fixed to it to prevent calcium chloride from falling between the turbine blades 24 into the adjacent compartment 52. An aluminum rod 85 with a diameter of 3 mm runs the length of the warmer, through the center of each partition 26 such that the partition 26 can be rotated in unison by use of a small hand crank 82 on the top of the warmer 10. The outer surface of the aluminum cylinder is anodized for blood compatibility and is covered with small aluminum ribs 79 in a spiral fashion, somewhat like the threads on a screw; however, each wind is discontinuous at 4 separate points circumferentially. These ribs protrude 0.5 to 1 mm from the uniformity of the conduit 22, to break up flow along the outside of the aluminum tube and prevent preferential flow down one side of the warmer.

The ribbed aluminum cylinder fits coaxially inside a slightly larger plastic cylinder such that the ribs fit snugly against the inner surface of the plastic cylinder. The space between the two cylinders, maintained by the aluminum ribs, is the conduit through which infusible solutions flow. This space is capped superiorly by a ring of fenistrated tubing continuous with a length of conventional blood tubing. A water tight seal exists between the ring of tubing, which communicates with the lumen of the conduit through the fenistrations in the capping ring. The fenistration are positioned solely on the inferior, or conduit, side of the ring. This blood tubing serves as the inflow line, through which cold solutions are introduced into the warmer.

The inferior end of the conduit ends in a shallow funnel, having an internal diameter about the same as that of the outer plastic cylinder. This is a water tight seal as well. The funnel communicates with another length of blood tubing which serves as the outflow of the warmer.

Another embodiment of the device (FIG. 7) includes a flexible device for warming the physiological fluids. The device is composed of a first container 58 enclosing a first compound 16 wherein said first compound 16 produces an exothermic chemical reaction in contact with the second compound 17, said first container 58 composed of friable material. A second container 55, said second container 55 having an inlet port 31 and an outlet port 34 and enclosing said first container 58. The second container 55 contains said second compound 17. A conduit 22 having an inlet 37 and outlet 40 positioned within said second container 55 and extending therethrough, said conduit 22 communicating with the exterior of said fluid-warming apparatus through the inlet port 31 and outlet port 34 of said second container 55.

Figure 7:
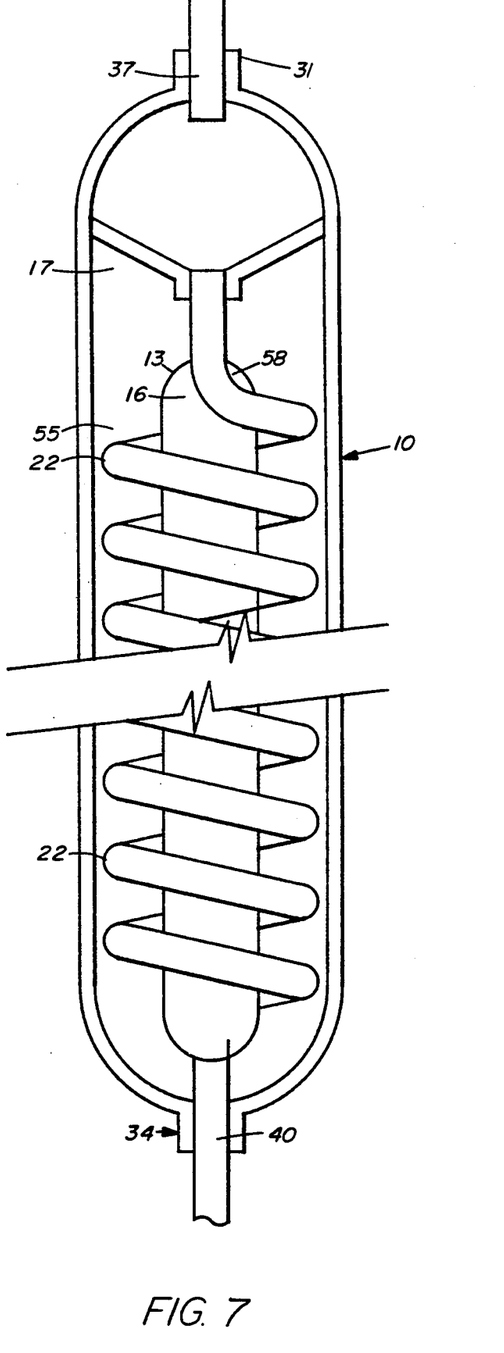
FIG. 7 shows a diagramatic view of flexible fluid warming device.

In the preferred embodiment, the conduit 22 is coiled about a longitudinal axis of the first container 58.

In the preferred embodiment, the second container 55 and said conduit 22 are composed of flexible nonbreakable materials. This provides for easy storage and handling.

Although not shown in the figures, the first container 58 can be a plurality of first containers, each of which contains a chemical 16. Said plurality of containers is each of small size such that breakage of the chemicals either sequentially or all at once can be used to regulate the amount of heat which is released.

In the flexible device, the first container 58 is made of friable or breakable material which can be easily shattered by mechanical stresses rupturing the container thus allowing the mixture of the two chemicals to produce the exothermic reaction. Blood again is passed from the inlet port 37 through the conduit 22 to the outlet port 40 and is heated as it passes through the length of conduit 22 in the container 10. The inlet 37 and outlet port 40 can be at opposite ends or at the same ends, again depending on how the coil is formed within the container 10. It is important that the materials be selected such that the first container 58 will rupture upon exposure to the mechanical stress, while the second container 55 and the conduit 22 are stable under the same stresses.

The only restriction on the first container 58 is that the material be easily rupturable and be composed of material that once disrupted does not create sharp fragments which would tear or disrupt the integrity of the conduit 22 or the second container 55.

In one embodiment said first container 58 is composed of a brittle material which brittle material will fracture upon bending or flexure. In another embodiment said first container 58 is composed of a relatively inelastic material and is suspended within a more elastic second container 55. In order to activate the exothermic reaction, the entire apparatus is flexed or stretched, which action causes the mechanical disruption of the integrity of the boundaries of the first container 58, thereby causing release of the contents 16 of the first container 58 into the second container 55.

In a preferred embodiment, said conduit 22 is a tube having a diameter of about 2 mm to 6 mm and is composed of a physiologically compatible material. In a most preferred embodiment said conduit 22 is flexible and wound in a helical configuration in the longitudinal axis of said first container.

In order to increase the surface contact of said conduit 22 with the fluid contents of said second container 55, thereby allowing for more rapid heat transfer to the fluid to be warmed within the conduit 22, the conduit 66 is most preferentially coiled for all or part of its length within said second container 55.

The flexible tubing of the conduit 22 is preferably tubing as that generally used for intravenous administration of fluids or medicaments to patients. Most preferably, the tubing is about 0.5 cm in diameter. The tubing may be of any substance compatible with the physiological fluids to be warmed and suitable for introduction of fluids into a patient. The coiled tubing should be of sufficient length to allow adequate surface area for heat transfer.

The second container 55 may be composed of any material that is flexible and physically stable in the presence of the reactants of the exothermic reaction. The composition of the second container 55 need not be indefinitely stable in the presence of both of the reaction reactants, but need be stable only as long as one would reasonably expect the device of the present invention to be in use. The composition of the second container should be such that it is stable at least in the presence of the second compound 17 for at least the shelf life of the apparatus. In the preferred embodiment the second container 55 is made of insulating material.

In the preferred embodiment, the device is of sufficiently small size such that it can be stored and used in a variety of environments, including by emergency medical technicians in the field, as well as in the hospital emergency room. The device is primarily designed for the rapid heating of infusable fluids for recussitation. The unit is designed to produce sufficient heat to warm approximately 4 to 6 units of packed cells. The useful lifetime of this device is approximately 20 to 30 minutes after activation. These limitations are of little consequence since almost all patients requiring hyperacute transfusions, especially out in the field or in the emergency room, will be either in the operating room or dead within the twenty minutes of arrival in the emergency center.

Additionally, all of the above described warming apparatus may further include a filter. Said filter can be positioned in line with the heat exchanger or conduit and preferably said filter is positioned at one end. Any blood filter which is known in the art can be adapted for use.

Figure 3:
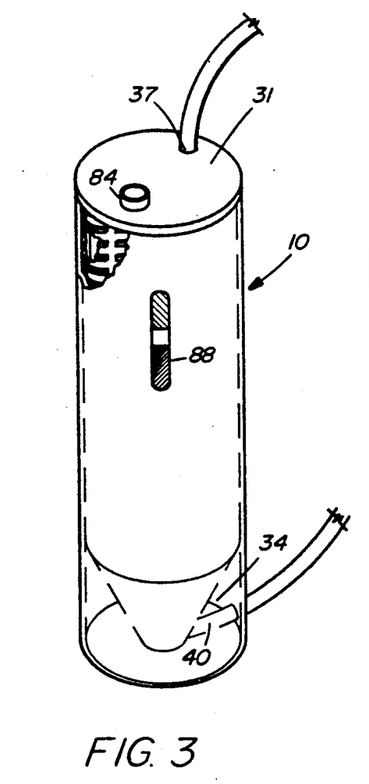
FIG. 3 is a diagramatic view of the device showing a temperature indicator.
Figure 4:
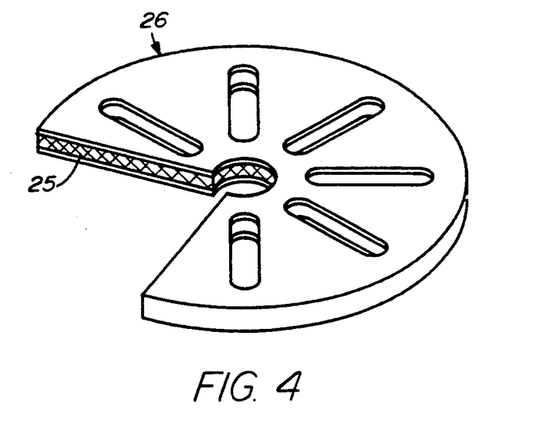
FIG. 4 is a diagramatic exploded view of a reaction container partition.
Figure 5:
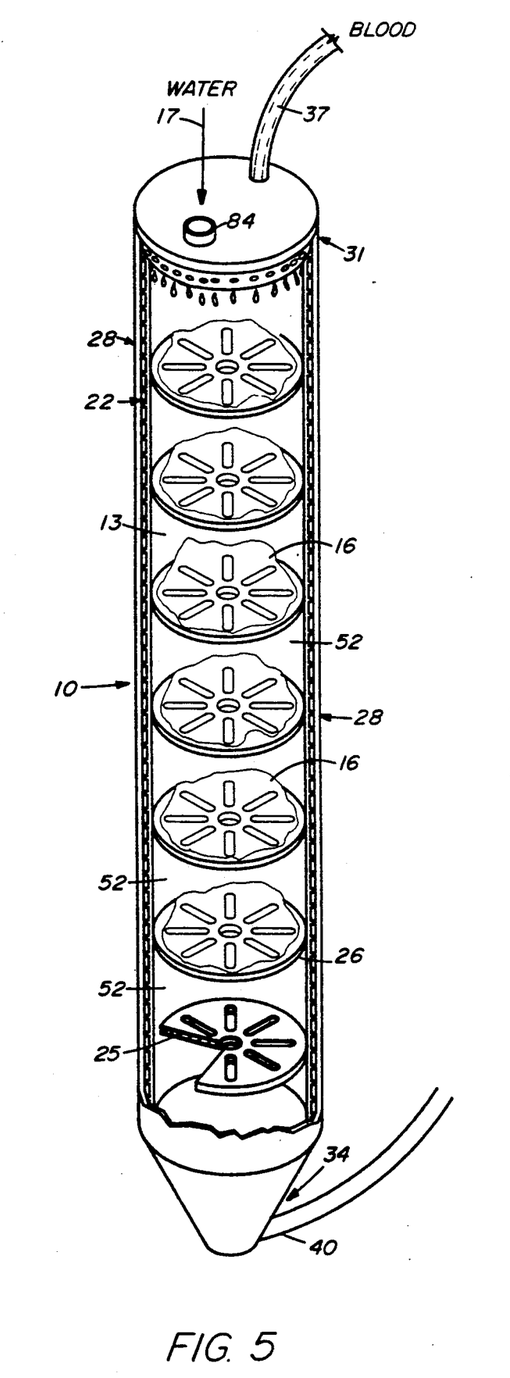
FIG. 5 is a diagramatic transverse section of the container.

A further addition to the device 10 can be the application of an indicator 88. Said indicator can be any material which measures temperature changes or use of the device 10. For example temperature sensitive liquid crystals can be incorporated into the device to monitor the temperature and use.

One skilled in the art will readily appreciate that the present invention is well adapted to carry out the objects and obtain the ends and advantages mentioned as well as those inherent therein. The device, compounds, methods, procedures and techniques described herein are presently representative of the preferred embodiments are intended to be exemplary and are not intended limitations on the scope. Changes therein and other uses will occur to those skilled in the art which are encompassed within the spirit of the invention or defined by the scope of the independent claims.

What is claimed is:

1. A portable, self-contained device for warming a physiological fluid comprising:

a reaction container capable of storing at least one chemical, said chemical capable of producing an exothermic chemical reaction when mixed with a second chemical;

a mixing means for mixing the first and second chemicals to produce said exothermic chemical reaction within said reaction container;

a heat exchanger having an inlet and outlet, said heat exchanger sufficiently close to said reaction container to absorb heat from said exothermic reaction and transfer said heat to the physiological fluid;

a temperature regulatory means in contact with said heat exchanger and said reaction container to regulate the maximum temperature of the device; and an insulating container for enclosing said reaction container, mixing means, heat exchanger and temperature regulatory means, said insulating container having an inlet port and an outlet port, wherein the inlet of the heat exchanger passes through the inlet port and the outlet of the heat exchanger passes through the outlet port.

2. The device of claim 1, wherein said temperature regulating means includes a composition of matter that undergoes a phase change at a temperature of between about 32° to 39° C.

3. The composition of matter of claim 2 wherein said matter is selected from the group consisting of waxes, polymers and crystalline solids.

4. The device of claim 1, further comprising a filter attached to one end of the conduit.

5. The device of claim 1 wherein, the first chemical is selected from the group consisting of anhydrous calcium carbonate, anhydrous calcium chloride, anhydrous calcium oxide, anhydrous sodium hydroxide and other anhydrous soluable salts; and the second chemical is water.

6. The device of claim 1, wherein said insulating container is composed of insulating material.

7. The device of claim 1, further comprising a temperature indicator.

8. The device of claim 1, further comprising more than one reaction container.

9. A method of rapidly heating stored cool physiological fluid to about 39° C. during infusion in a portable, self-contained device, comprising the steps of:

activating the device by mixing in a reaction container first and second chemicals to produce an exothermic chemical reaction; and passing the physiological fluid through a heat exchanger in said device prior to infusion, wherein said heat exchanger is sufficiently close to said reaction container to absorb heat from said exothermic reaction and transfer said heat to the physiological fluid and wherein a temperature regulatory means is in contact with said heat exchanger and said reaction container to regulate the temperature of the device.

10. The method of claim 9, wherein said physiological fluid is blood.

11. A portable self-contained device for warming blood comprising:

a reaction container capable of storing separately at least a pair of chemicals, said chemicals producing an exothermic chemical reaction when mixed;

a mixing means integral with said reaction container for mixing at least a pair of chemicals;

a conduit having an inlet and an outlet said conduit coiled around said reaction container;

a temperature regulating means having a phase change reaction temperature of between 34° to 39° C., said temperature regulating means coating said reaction container and said conduit and forming a layer between said reaction container and said conduit;

an insulating container enclosing the reaction container, at least a pair of chemicals, the conduit, the mixing means and the temperature regulation means, said insulating container having inlet and outlet ports, wherein one open end of said conduit passes through the inlet port, and the other end of said conduit passes through the outlet port.

12. The device of claim 11, wherein said temperature regulating means is selected from the group consisting of waxes, polymers and crystalline solids.

13. The device of claim 11, further comprising a temperature indicator.

14. The device of claim 11, further comprising more than one reaction container.

15. The device of claim 11, further comprising, a filter for filtering the blood, wherein said filter is attached to one end of the conduit.

16. A method of rapidly heating stored cooled blood up to about 37° C. prior to infusion in a portable self-contained device, comprising the steps of:

activating the device by mixing at least a pair of chemicals in the device between a conduit and reaction container to produce an exothermic chemical reaction; and passing the blood through the conduit in said device, wherein there is a temperature regulating means having a phase change reaction temperature of between 34° to 39° C., said temperature regulating means coating said conduit and transferring heat from the exothermic reaction to the blood.

17. A device for warming physiological fluids comprising:

a first container enclosing a first reactant wherein said first reactant produces an exothermic chemical reaction when contacted with a second reactant said first container composed of friable material;

a second container having an inlet port and outlet port and enclosing said first container and containing said second reactant;

a conduit having an opening at each end positioned within said second container and extending therethrough, said conduit communicating with the exterior of said fluid warming apparatus through the inlet port and outlet port of said second container.

18. The apparatus of claim 17 wherein said conduit is coiled about a longitudinal axis of the second container.

19. The apparatus of claim 17 wherein said second container and said conduit are composed of flexible material.

20. The apparatus of claim 17 having a plurality of first containers.

* * * * *